United States Patent [19]

Hoess et al.

[11] Patent Number: 5,573,922
[45] Date of Patent: Nov. 12, 1996

[54] IMMUNOLOGICAL DETECTION METHOD FOR TRIAZINES

[75] Inventors: Eva Hoess, Starnberg; Erasmus Huber, Finning; Christine Markert-Hahn, Seeshaupt; Wolfgang Rollinger, Polling, all of Germany

[73] Assignee: Boehringer Mannheim GmbH, Mannheim, Germany

[21] Appl. No.: 235,393

[22] Filed: Apr. 29, 1994

[30] Foreign Application Priority Data

Apr. 29, 1993 [DE] Germany .......................... 43 14 091.2

[51] Int. Cl.⁶ ................................................ G01N 33/545
[52] U.S. Cl. ........................................ 435/7.93; 436/815
[58] Field of Search ........................... 435/7.93; 436/815

[56] References Cited

U.S. PATENT DOCUMENTS 4,530,786  7/1985 Dunbar et al. ........................ 436/819

FOREIGN PATENT DOCUMENTS 0180305  7/1986  European Pat. Off. ..
0300381  1/1989  European Pat. Off. ..
0365818  5/1990  European Pat. Off. ..

OTHER PUBLICATIONS

Vom Wasser, Bd. 75, pp. 115–126, "ELISAs for the Analysis of Atrazine and Atrazine Metabolites in Water", 1990.

Harrison et al., *Journal of Agricultural and Food Chemistry*, Bd. 39, Nr. 1, 1991, "Competitive Inhibition ELISA for the S–triazine Herbicides: Assay Optimization and Antibody Characterization", Wash, DC., pp. 122–128.

Wittmann et al., *Journal of Agricultural and Food Chemistry*, Bd. 39, Nr. 6, 1991, "Development of an ELISA for the Analysis of Atrazine Metabolites Deethylatrazine and Deisopropylatrazine", Wash., DC., pp. 1194–1200.

Dunbar et al., *Journal of Agricultural and Food Chemistry*, Bd. 39, Nr. 2, 1990, pp. 433–437, "Development of Enzyme Immunoassay for the Detection of Triazine Herbicides", Wash., DC.

Huber et al., *Zeitschrift Für Pflanzenkrankheiten Und Pflanzenschutz*, Bd. 92, Nr. 2, 1985, pp. 147–156, "A Solid–phase Enzyme Immunoassay for Quantitative Determination of the Herbicide Terbutryn", Stuttgart, DE.

P. Kramer et al., Pestic. Sci., vol. 32, No. 4, pp. 451–462 (1991).

C. Wittmann et al., Vom Wasser, vol. 75, pp. 115–126 (1990).

C. Wittmann et al., Food Agric. Immunol., vol. 1, No. 4, pp. 211–224 (1989).

A. Lucas et al., Food Agric. Immunol., vol. 3, No. 3–4, pp. 155–167 (1991).

A. Lucas et al., Chem. Res. Toxicol., vol. 6, No. 1, pp. 107–116 (1993).

U. Obst, "Application of Molecular Biological Methods in Water Analysis using Spectrometric Detection", *GIT Fachz. Lab.* 4 (1992) 365.

R. Reupert, "Analytical Method for the Determination of Pesticides by Micro–HPLC", *GIT Spezialchromatographie* 1 (1992) 30–36.

L. Weil, "Die Problematik der Spurenanalytik, von Pflanzenschutzmitteln im Trinkwasser und in Gewässern", *Nachr. Chem. Techn. Lab.* 39 (1991) 1277.

B. Dunbar et al., "Development of Enzyme Immunoassay for the Detection of Triazine Herbicides", *J. Agric. Food Chem.* 38 (1990) 433–437.

M. H. Goodrow et al., "Hapten Synthesis, Antibody Development, and Competitive Inhibition Enzyme Immunoassay for s–Triazine Herbicides", *J. Agric. Food Chem.* 38 (1990) 990–996.

S. Wüst et al., "Sensitive s–Triazine Enzyme Immunoassay for Water Samples in Polysterene Tubes", *GIT Fachz. Labor* 2 (1990) 99.

S. J. Huber et al., "Solid–Phase Enzyme Immunoassay for the Determination of Herbicides from Fresh Water—Polystyrene Spheres in Comparison to Microtiter Plates as Antibody Carriers", *GIT Fachz. Labor*, 10 (1985) 969.

*Primary Examiner*—Mary E. Ceperley
*Attorney, Agent, or Firm*—Nikaido, Marmelstein, Murray & Oram LLP

[57] ABSTRACT

An immunological method for the determination of triazine and triazine derivatives by a competitive immunoassay in which the sample and labelled atrazine compete for a polyclonal antibody which is bound to a solid phase before, during or after the immunological reaction, the immunological complex binds to the solid phase, the solid phase and unbound labelled atrazine are separated and the label in the solid or liquid phase is determined as a measure of the content of triazine and triazine derivatives, which is characterized in that polyclonal antibodies which were obtained by immunization with a 4-alkylamino-S-triazine are used and a conjugate of a label and 4-amino-S-triazine which is bound to the label via the 6 position is used as the labelled atrazine. Triazine and triazine derivatives can be determined simultaneously using this method.

12 Claims, No Drawings

IMMUNOLOGICAL DETECTION METHOD FOR TRIAZINES

The invention concerns an immunological method for the detection of triazines as well as the reagents used for this.

Triazines and triazine derivatives such as atrazine, simazine, ametryn, propazine, terbutylazine, cyanazine, desethylterbutylazine are substances which are used as herbicides on a large scale in plant protection. Since triazines are only degraded very slowly in soil and can thus enter into the ground water, a rapid and sensitive test for triazines is of particular importance.

The determination of triazines is carried out either by instrumental analysis (HPLC or GC-MS methods, U. Obst, "GIT Fachz. Lab." 4 (1992) 365), microbiologically (R. Reupert, "GIT Spezialchromatographie" 1 (1992, 30) or by immunological detection methods (Achr. Chem. Tech. Lab. 39 (1991) M1–M42).

The immunological detection methods for triazines are preferably carried out as an ELISA test. This is usually a competitive test in which an antibody against a triazine or triazine derivative is immobilized and the triazine from the sample competes with a conjugate of triazine and a label which is preferably an enzyme. The more triazine is present in the sample, the less enzyme-labelled conjugate is bound to the antibody. After formation of the immunological complexes, the amount of the enzyme label is determined, usually photometrically, as a measure of the amount of triazine present in the sample.

Such immunoassays can be used to determine either individual triazines or whole groups of triazines. In the known immunoassays it is usual to use monoclonal antibodies (for tests for individual triazines) or polyclonal antibodies (for tests for individual triazines or triazine groups) as well as a conjugate of an enzyme, preferably peroxidase, and the hapten which is also used for the immunization (homologous conjugate). A homologous enzyme conjugate is thus a conjugate of hapten and enzyme in which the hapten in the conjugate and immunogen are identical with regard to the pattern of substituents and coupling position of the activated hapten.

Although it is possible to detect atrazine with a high sensitivity using the known group-specific triazine tests, the sensitivity towards other triazines is, however, low (L. Weil, "Nachr. Chem. Tech. Lab." 39 (1991) 1277).

An immunological detection method for triazines is known from EP-A 0 300 381 in which polyclonal antibodies from rabbits as well as an enzyme conjugate of alkaline phosphatase and a triazine, which is selected according to the type of antibody, are used. If the test is carried out with an antibody which has been produced by immunization with ametryn, then ametryn is used in the conjugate.

A method for the determination of atrazines is known from EP-B 0 180 305 in which likewise the same hapten is used for the immunization as in the enzyme conjugate. Analogous tests are described by B. Dunbar, J. Agric. Food Chem. 38 (1990) 433–437, M. H. Goodrow, J. Agric. Food Chem. 38 (1990) 990–996. In these references it is also stated that such homologous conjugates (in which the triazine is bound to the carrier protein for the immunization and to the enzyme in the conjugate at the same site) give better results in the test than when a heterologous conjugate (in which binding of the immunological carrier and enzyme is via different positions on the triazine ring) is used.

However, only a low sensitivity is achieved for some triazines using the known tests so that it cannot be established whether the contamination of the sample with triazines as a whole is below the value prescribed by law. Hence the known immunological tests do not ensure a complete determination of all triazine derivatives in water samples.

The object of the present invention is therefore to provide a method for the determination of triazine and triazine derivatives which can be used to screen water samples contaminated with triazines, which achieves a high sensitivity and cross-reactivity to atrazine, ametryn, propazine, terbutylazine, simazine, cyanazine and desethylterbutylazine and with which it is possible to detect amounts at the legal limits of 0.1 µg/l atrazine and 0.5 µg/l mixture of triazines.

The object of the present invention is achieved by an immunological method for the determination of triazine and triazine derivatives by a competitive immunoassay in which the sample and labelled atrazine compete for a polyclonal antibody which is bound before, during or after the immunological reaction to a solid phase, the immunological complex binds to the solid phase, the solid phase and unbound labelled atrazine are separated and the label is determined in the solid or liquid phase as a measure of the content of triazine and triazine derivatives which is characterized in that polyclonal antibodies which were obtained by immunization with a 4-alkyl-amino-S-triazine are used and a conjugate of a label and 4-amino-S-triazine which is bound to the label via the 6 position is used as the labelled atrazine.

It surprisingly turned out that a high cross-reactivity of the method of determination for atrazine, terbutylazine, desethylterbutylazine, propazine, simazine, cyanazine, desethylatrazine and desisopropylatrazine is achieved by combining polyclonal antibodies and conjugates produced in this way.

In this way it is also possible to determine atrazine and atrazine derivatives.

In contrast there is a substantially weaker cross-reactivity when using a homologous conjugate (hapten in the immunogen and conjugate is identical).

Triazines are used as immunogens which carry an alkylamino residue in the 4 position and are bound to the immunogenic carrier via the 6 position. Short-chained, branched and unbranched alkyl residues with 1–4 C atoms are used as alkyl residues. An isopropyl residue is particularly preferably used.

Coupling to the immunogenic carrier (e.g. KLH, β-galactosidase, edestin) is preferably carried out by nucleophilic substitution. For this a substituted amino group is introduced whose substituent is suitable for coupling to the immunological carrier. For example a carboxyl group is introduced as the activated group which is activated to form a hydroxysuccinimide and is subsequently coupled via the amino group of the immunological carrier. Further methods of coupling are familiar to a person skilled in the art (M. Brinkley, Bioconjugate Chem. 3 (1992) 2–13).

The production of the polyclonal antiserum is also carried out according to conventional methods familiar to a person skilled in the art and preferably in sheep. Such an immunization is described for example by B. Dunbar, J. Agric. Food Chem. 38 (1990) 433–437 and N. H. Goodrow, J. Agric. Food Chem. 38 (1990) 990–996. The polyclonal antisera obtained can be used without further purification.

Any label familiar to a person skilled in the art can be used as the label in the conjugate of label and triazine derivative. However, an enzyme label (peroxidase, alkaline phosphatase, β-galactosidase) is preferably used. The triazine derivative is coupled to the enzyme via the 6 position. In order to produce these conjugates, a chloro-nucleophilic substitution is firstly carried out at the 6 position via the amino group of a heterobifunctional spacer. Any group which can be activated can be used as the second functional group of the spacer. However, a thiol group which is S-acetyl-protected is preferably used. The length of the spacer between triazine and peroxidase is not critical, however, it is expedient that it is between 10 and 30 atoms. In a further reaction step the chlorine in the 4 position is then substituted by an amino group. Subsequently the protected thiol group is released and it is expedient to couple the triazine and enzyme via a maleinimido-functionalized enzyme.

The immunological determination of triazine and triazine derivatives is carried out according to methods familiar to a person skilled in the art. Such methods are for example described in S. Wüst, "Git Fachz. Labor" 2 (1990) 99, S. J. Huber, "Git Fachzt. Labor" 10 (1985) 969, B. Dunbor, JU. Agric. Food Chem. 38 (1990) 433, M. H. Goodrow, J. Agric. Food Chem. 38 (1990) 990. For this the polyclonal antiserum is usually bound to a carrier such as microtitre plates. This binding can be absorptive, covalent or via an additional binding pair such as for example biotin/avidin. In the latter case streptavidin is for example immobilized on a microtitre plate and the antibodies of the polyclonal antiserum are coupled to biotin. The determination is carried out by adding the sample and conjugate of atrazine derivative and label to the immobilized or immobilizable polyclonal antibodies. After incubation, the liquid and solid phases are separated and the label is determined in the solid or separated liquid phase. An enzyme label is preferably used. In this case the test is preferably carried out by means of a subsequent chromogenic reaction. If peroxidase is used as an enzyme, it is expedient to carry out the detection reaction by means of ABTS® or similar $H_2O_2$ detection systems.

The invention is elucidated further by the following examples:

EXAMPLE 1

Production of the triazine immunogen

Example 1.1

2,4-Dichloro-6-tert.butylamino-1,3,5-triazine 10 ml 0.1N sodium hydroxide solution and 6.74 g (92.25 mmol) tert.butylamine are added to 9.23 g (50 mmol) cyanuric chloride in 200 ml toluene and stirred for 1 hour at 20° C. The pH value of the reaction is monitored continuously during this period and if necessary readjusted to pH 11–12 with 1N sodium hydroxide solution. Subsequently the solvent is removed by distillation, the residue is taken up in 150 ml water, extracted twice with 150 ml ethyl acetate each time, the organic phase is dried over magnesium sulfate and the solvent is removed. The residue is dissolved in 200 ml ethyl acetate/petroleum ether (v/v 4/1), insoluble components are removed by filtration and the filtrate is concentrated by evaporation. The crude product is purified by column chromatography (silica gel Merck 60, 5×30 cm, eluant: ethyl acetate/petroleum ether (v/v 4/1).

Yield: 8.84 g (74% of theoretical yield)

$^1$H—NMR ($D_6$—DMSO/TMS): 1.36 (s, 9H, C$\underline{H}_3$); 8.91 ppm (s, 1H, N$\underline{H}$).

TLC: silica gel (Merck 60), ethyl acetate/petroleum ether (v/v 4/1).

$R_f$=0.88

Example 1.2

6-[N-(6-Aminohexylcarboxyl)]-2-chloro-4-tert.butylamino-1,3,5-triazine 5.25 g (40 mmol) 6-aminocaproic acid in 20 ml 0.1N sodium hydroxide solution is slowly added dropwise to a solution of 4.42 g (20 mmol) of the compound from example 1.1 in 100 ml toluene. The pH value is readjusted to pH 11–12 with 1N sodium hydroxide solution and the reaction mixture is kept under reflux for 3 hours. Subsequently the solvent is removed in a water-jet vacuum, the residue is dissolved in a small amount of THF and slowly added dropwise to 500 ml ice-cooled diisopropyl ether. The suspension is stirred for a further 30 minutes while cooling on ice, the precipitate is filtered by suction and dried in a high vacuum.

Yield: 0.76 g (6% of theoretical yield)

$^1$H—NMR ($D_6$—DMSO/TMS): 1.34 (s, 9H, C$\underline{H}_3$), 1.48 (m, 6H, C$\underline{H}_2$); 2.12 (t, 2H, J=7.0 Hz, C$\underline{H}_2$—COOH); 3.17 (m, 2 H, C$\underline{H}_2$—NH); 7.39 (s, br, 1H, N$\underline{H}$—C); 7.75 ppm (m, 1H N$\underline{H}$—CH$_2$); COOH exchange under the recording conditions.

TLC: silica gel (Merck 60), ethyl acetate/methanol (v/v 3/1) and 1% acetic acid.

$R_f$=0.77

Example 1.3

Methanesulfonic acid-N-hydroxysuccinimide ester 1.15 g (10 mmol) N-hydroxysuccinimide is dissolved in 10 ml anhydrous THF and admixed slowly with 1.6 ml triethylamine. The suspension that forms is cooled with an ice/sodium chloride mixture and 0.78 ml (10 mmol) methansulfonyl chloride is added at 0°–5° C. while stirring. It is stirred for a further 30 minutes at 0° C., afterwards the temperature is allowed to increase to 20° C. The mixture is allowed to stand overnight at 20° C. and is subsequently concentrated by evaporation in a vacuum. The crystallized residue is taken up in water, filtered by suction and washed well with water. The product is dried over Sicapent in a dessicator until the weight remains constant.

Yield: 1.63 g (84% of theroretical yield)

Example 1.4

Activated triazine hapten 633 mg (2 mmol) of the compound from example 1.2 is suspended in 30 ml methanol and admixed with 113.4 mg (1.6 mmol) solid potassium hydroxide. The clear solution which forms is stirred for 20 minutes at 20° C. and subsequently the solvent is removed by distillation in a water-jet vacuum. The residue is taken up in 20 ml THF, 386.3 mg (2 mmol) methanesulfonic acid-N-hydroxysuccinimide ester from example 1.3 and catalytic amounts of dibenzo-18-crown-6 are added and it is stirred for 21 hours at 20° C. The solvent is removed by distillation, the residue is taken up in 50 ml ethyl acetate and insoluble material is removed by filtration. The filtrate is extracted once with 50 ml saturated sodium bicarbonate solution and twice with water, dried over magnesium sulfate and concentrated by evaporation in a high vacuum.

Yield: 710 mg (86% of theoretical yield)

$^1$H—NMR ($D_6$—DMSO/TMS): 1.37 (s, 9H, C$\underline{H}_3$); 1.40 (m, 2H, C$\underline{H}_2$); 1.53 (m, 2H, C$\underline{H}_2$); 1.64 (m, 2H, C H$_2$); 2.65 (t, 2H, J=7.0 Hz, CH$_2$—COO); 2.82 (s, 4H, CH$_2$COO); 3.33 (m, 2H, CH$_2$—NH); 7.45 (s, 1H, N H—C); 7.80 ppm (t, 1H, J=6.8 Hz, NH—CH$_2$).

$^{13}$C—NMR (D$_6$—DMSO/TMS): 23.88, 25.23 (CH$_2$); 25.35 (CH$_3$); 28.10, 30.08 (CH$_2$); 39.40 (CH$_2$—NH); 50.50 (C—(CH$_3$)$_3$); 164.56, 164.89 (N=C—N); 167.23 (C—Cl); 168.74 (COO); 170.07 ppm (O CO—CH$_2$).

MS (EI): 412 [M]$^+$

TLC: silica gel (Merck 60), ethyl acetate/methanol (v/v 3/1). R$_f$=0.91

Example 1.5

Triazine immunogen 157 mg (3.8×10$^{-4}$ mol) of the compound from example 1.2 in 20 ml dioxane is added dropwise to a solution of 4 g (2.1×10$^{-6}$ mol, 1 g β-gal active substance) β-galactosidase lyophilisate in 100 ml water and adjusted to pH 8.5–9.0 with 0.1N sodium hydroxide solution. After 30 minutes the pH value is readjusted to pH 8.5–9.0 and the mixture is stirred for a further 16 hours at 20° C. Subsequently the reaction solution is concentrated in an Amicon cell and 50 ml 10 mmol KPO$_4$ buffer pH 7.0 containing 0.9% sodium chloride is added. The immunogen is purified over an AcA 202 gel column (3×50 cm, eluant: 10 mmol KPO$_4$ buffer pH 7.0 containing 0.9% sodium chloride). The fractions of the first peak (UV detector, 280 nm) are pooled.

EXAMPLE 2

Production of the homologous POD conjugate

Horseraddish peroxidase (PODp)[1] is dissolved in 10 mM potassium phosphate buffer pH 8.5, 0.1M NaCl, 0.25 mM CaCl$_2$ and the activated triazine hapten from 1.3 is dissolved in DMSO. The appropriate amounts of PODp and triazine are mixed so that a molar stoichiometry of 5:1 (hapten:protein) results. The DMSO concentration in the coupling is 20%. The incubation is carried out for 2 hours at 25° C. while stirring. Subsequently it is dialysed overnight against 10 mM potassium phosphate buffer, pH 7.0, 0.1M NaCl, 0.025 mM CaCl$_2$ to separate the non-reacted hapten.

[1] Pre-polymerized POD (PODp) can be obtained by reacting monomeric POD with glutardialdehyde as described by Engvall and Perlmann (Immunochemistry 8 (1971), 871–874).

EXAMPLE 3

Production of the heterologous triazine conjugate

Example 3.1

1-Butoxycarbonyl-1,2-diaminoethane (m-Boc-ED)

Intermediate product 218 g (1 mol) di-tert.butyldicarbonate in 1 l dioxane is added dropwise within 1 hour to a solution of 120 g (2 mol) ethylene diamine and 2 l dioxane/water (v/v 1/1) while stirring at 0° C. After stirring for 1 hour at 20° C., the solvent is concentrated by evaporation in a water-jet vacuum, the bis-1,2-butoxycarbonyl-1,2 diaminoethane which formed as a by-product is removed by filtration and the filtrate is extracted with 300 ml ethyl acetate. The organic phase is washed a further three times with 100 ml water each time, dried over sodium sulfate and concentrated by evaporation in a water-jet vacuum.

Yield: 27.3 g (8.5% of theoretical yield)

$^1$H—NMR (CDCl$_3$/TMS): 1.45 (s, 9H, O—C(CH$_3$)$_3$); 2.79 (T, 2H, J=7.5 Hz, CH$_2$—NH); 3.14 (m, 4H, CON H) 5.00 ppm (s, br, 1H, O—CH$_2$—NH$_2$);

TLC: silica gel 60 (Merck), isopropanol/butyl acetate/water/ammonia (v/v/v/v 50/30/15/5), detection with ninhydrin.

R$_f$=0.23

Example 3.2

1-Butoxycarbonyl-2-[(3-methylcarbonylthio)-propionyl-]-1,2-diaminoethane (Boc-ED-(S)ATP)

8.00 g (50 mmol) of the compound from example 3.1 and 12.26 g (50 mmol) N-succinimidyl-S-acetylthiopropionate (SATP) are dissolved in 100 ml tetrahydrofuran and stirred for 4 hours at 20° C. Subsequently the solution is cooled in an ice bath, the precipitated product is filtered by suction and dried in a high vacuum at 40° C.

Example 3.4

6-[N-[3-Methylcarbonylthio)-propionyl]-1,2-diaminoethyl]-2,4-dichloro-1,3,5-triazine (Dichlorotriazine-ED-(S)ATP)

1.52 g (5 mmol) 1-[(3-methylcarbonylthio]-propionyl]-1,2-diaminoethanetrifluoroacetate salt (ED-(S)ATPXTFA) from example 3.3 is dissolved in 50 ml tetrahydrofuran/dioxane (v/v 1/4) and 0.51 mg (0.70 ml, 5 mmol) triethylamine is added. The reaction mixture is subsequently cooled to 0° C. and 0.92 g (5 mmol) cyanuric chloride and 0.51 mg (0.70 ml, 5 mmol) triethylamine is added. During the 3 hour stirring while cooling on ice the pH value of the reaction mixture is monitored and if necessary is readjusted with triethylamine to pH 6. The precipitate is separated and the solvent is removed without heating by distillation in a high vacuum. The residue is dissolved in a small amount of ethyl acetate/hexane (v/v 9/1) and purified by means of column chromatography [silica gel 60 (Merck) 4×11 cm, eluant: ethyl acetate/hexane (v/v 9/1)].

Yield: 935 mg (55.3% of theoretical yield)

$^1$H—NMR (D$_6$-acetone/TMS): 2.27 (s, 3H, CH$_3$); 2.45 (t, 2H, J=7.0 Hz, CH$_2$S); 3.07 (t, 2H, J=7.0 Hz); 3.53 (m, 4H); 7.30 ppm (s, br, 1H, NH).

$^{13}$C—NMR (D$_6$-acetone/TMS): 25.4 (CH$_2$S); 30.5 (CH$_3$); 36.4 (CH$_2$CO); 39.1 and 42.4 (CH$_2$N); 170.3 and 171.2 (triazine ring); 171.9 (CONH); 195.6 ppm (CSNH).

Yield: 9.22 g (63.9% of theoretical yield).

Example 3.3

1-[(3-Methylcarbonylthio)-propionyl]-1,2-diaminoethanetrifluoroacetate (ED-(S)ATP×TFA)

7.25 g (25 mmol) of the compound from example 3.2 is dissolved in 10 ml trifluoroacetic acid and stirred for 4 hours at 20° C. Subsequently the solution is evaporated to dryness in a water-jet vacuum and the residue is digested with 50 ml diisopropyl ether. The product is dried in a high vacuum and crystallizes after a long induction phase.

Yield: 5.54 g (65% of theoretical yield)

$^1$H—NMR (D$_6$—DMSO/TMS): 2.31 (s, 3H, —CH$_3$); 2.39 (t, 2H, J=7.0 Hz, CH$_2$—CO); 2.85 (t, 2H, J=7.0

Hz, C$\underline{H}_2$S); 3.00 (t, 2H, J=7.0 Hz, C$\underline{H}_2$NH); 3.26 (t, 2H, J=7.0 Hz, C$\underline{H}_2$NH); 7.92 (s, br, NH); 8.13 ppm (s, br, 1H, N$\underline{H}$—CO)

TLC: silica gel 60 (Merck), ethyl acetate/glacial acetic acid/water (v/v/v 5/5/2), detection with ninhydrin. $R_f$=0.62

TLC: silica gel 60 (Merck), ethyl acetate/hexane (v/v 9/1). $R_f$=0.57

Example 3.5

Activated triazine hapten 17 ml of a dioxane/ammonia solution (1 l dioxane contains 0.6 mol $NH_{3gas}$, 17 ml=10 mmol) is added to 338 mg (1 mmol) of the compound from example 3.4. After stirring for 6 hours at 20° C., the solvent is removed in a water-jet vacuum and the residue is purified by means of preparative HPLC (water/acetonitrile 0.1% TFA).

Yield: 126 mg (34% of theoretical yield)

$^1$H—NMR (D$_6$—DMSO/TMS): 2.31 (s, 3H, C$\underline{H}_3$); 2.36 (t, 2H, J=6.9 Hz, C$\underline{H}_2$—S); 2.99 (t, 2H, J=6.9 Hz, C$\underline{H}_2$CO); 3.21 (m, 4H, C$\underline{H}_2$NH); 7.33 (s, br, 2H, N$\underline{H}_2$); 7.66 (t, br, 1H, J=7.0 Hz, N$\underline{H}$); 8.03 ppm (t, br, 1H, J=7.0 Hz, N$\underline{H}$).

$^{13}$C—NMR (D$_6$—DMSO/TMS): 24.4 (CH$_2$—S); 30.5 (C$\underline{H}_3$CO); 34.8 (C$\underline{H}_2$CO); 38.0 39.6 (C$\underline{H}_2$NH); 165.5, 166.8, 168.8 (N=$\underline{C}$—N); 170.2 (C$\underline{O}$NH); 195.5 ppm (C$\underline{O}$S).

FAB-MS: 319 [M+H]$^+$

TLC: silica gel 60 (Merck), ethyl acetate/methanol (v/v 9/1).

$R_f$=0.61

Example 3.6

Atra(Deethyl-4-ED)-SATP-PODp(MH)

In order to activate the PODp, the PODp is reacted with MHS (maleimido-hexanoyl-N-hydroxysuccinimide ester) in a molar ratio of 20:1 (hapten to protein). The excess MHS is then removed by dialysis. A hydroxyl-aminolysis is carried out in order to release the protected SH groups in the hapten (0.1M potassium phosphate buffer pH 8.0, 0.1M hydroxylamine final concentration, at 25° C. within 1 hour). For the coupling, the maleinimido-activated PODp is dissolved in 0.01M potassium phosphate buffer, pH 6.2, 50 mM NaCl, 1 mM EDTA and mixed with the appropriate amount of activated hapten so that a molar stoichiometry of 1:1 results. The DMSO concentration in all solutions containing activated hapten should be 20% since otherwise the hapten precipitates. The coupling mixture is incubated for 1.5 hours at 25° C. Subsequently the MH groups which are still free on the POD are saturated with 1/100 of the volume of 0.2M cysteine solution (30 minutes, 25° C.). In order to separate the lower molecular components, the coupling mixture is dialysed overnight against 10 mM potassium phosphate buffer pH 7.0, 0.1M NaCl, 0.025 mM CaCl$_2$.

EXAMPLE 4

Immunization and testing of the antisera 10 sheep are immunized with triazine immunogen according to example 1 in Freund's adjuvant. The dose is 500 g per animal. The immunizations are repeated over six months or longer, each at intervals of 4 weeks. Antiserum samples are taken from all animals once per month and examined for the presence of triazine antibodies. For this purpose a series of terbutylazine standards are measured in a competitive ELISA using the heterologous POD conjugate atra(deethyl-4-ED)-SATP-POD(MH) according to example 3. The procedure for this measurement is described in detail in example 5.

Those antisera are selected as being suitable which yield an adequately high measurement signal (at least 1000 mA after 30–60 min. colour development) and which react well with terbutylazine (50% displacement with less than 300 ng/ml terbutylazine).

EXAMPLE 5

Determination of the concentration of various triazines

Solutions used

Coating buffer: 50 mM sodium bicarbonate; 0.1 % sodium azide; pH 9.6

Incubation buffer: 10 mM sodium phosphate; 0.1% Tween 20 (Brenntag Comp., Order No. 460761); 0.9% NaCl; 1% crotein C (CRODA GmbH, Order No. 38241422); pH 7.4

Washing solution: 0.9% NaCl; 0.1% Tween 20

Substrate solution: substrate solution Enzymun (Boehringer Mannheim GmbH, Order No. 857424), containing 1.9 mM ABTS and 3.2 mM sodium perborate in phosphate-citrate buffer pH 4.4) with 2 mg/ml vanillin Procedure Coating:

Microtitre plates (Maxisorp F96,Nunc Co. Order No. 4-42404) are coated with antibodies against the Fc part of sheep IgG which have been obtained by immunosorptive purification of the IgG fraction from donkey antiserum. The donkey antibody is dissolved in the coating buffer at a concentration of 10 g/ml protein and 100 µl of this solution is pipetted into each well of the microtitre plate. After incubating for 1 hour at room temperature while shaking, the solution is discarded and the plate is washed three times with washing solution.

Binding of the triazine antibodies:

Sheep antiserum against triazine is diluted 1:50,000 with incubation buffer. Each well of the microtitre plate is coated with 100 µl of the diluted solution. During the incubation period (1 hour, conditions as above) the IgG molecules from the sheep serum bind to the donkey antibodies bound to the wall. They are subsequently washed as above.

Reaction with triazines and triazine-POD conjugate:

A series of solutions is prepared which contain terbutylazine at concentrations of 1000/500/250/125/62.5/31/16/8/4/0 ng/l as well as the conjugate atra(deethyl-4-ED)-SATP-PODp(MH) according to the invention at a standard concentration of 50 mU/ml in the incubation buffer.

Dilution series of other triazines are prepared in a similar manner with maximum concentrations of 1000 ng/ml (atrazine, cyanazine and desethylterbutylazine), 10,000 ng/l (propazine, simazine, desethylatrazine) and 100,000 ng/l (desisopropylatrazine) and dilution steps of 1:2 which also contain the said hapten-POD conjugate.

The wells of the microtitre plate which were precoated as previously described, are filled with these solutions (100 μl in each case), incubated for 1 hour and subsequently washed as described.

The free hapten molecules compete with the hapten-POD conjugate for the limited amount of hapten-specific antibodies on the the wall of the wells. The less conjugate is bound the more free hapten is present in the solution and the better the hapten is recognized by the antibodies.

Substrate reaction:

Every well is filled with 100 μl substrate solution and incubated while shaking until the colour development in the samples without hapten appears subjectively to be high enough. Then the absorbance in all wells is determined as a differential measurement at the wavelengths 405/492 nm.

Evaluation:

In the graph of the measured signal as a function of the hapten concentration used, the "relative affinity", i.e. the hapten concentration whose measured signal is half the size of the maximum signal (at a hapten concentration of 0), is determined for each triazine compound. In this process a linear interpolation is made between selected measurement points on the curve. This gives the cross-reaction of the triazines in relation to terbutylazine as the quotient $$\frac{\text{relative affinity terbutylazine}}{\text{relative affinity triazine } XY} \times 100\%$$

The "lower limit of detection" is determined in an analogous manner for each triazine compound as the concentration at which the measured signal is 80% of the maximum signal.

In a second experiment the cross reaction and the lower limit of detection for each of the above-mentioned triazines is determined in an analogous manner using the homologous conjugate atra(terbutyl-6ah)-OSu-POD. In this case the POD concentration is 30 mU/ml. The highest hapten concentrations are 10,000 ng/l for terbutylazine and 100,000 ng/l for all triazines.

Eight further hapten concentrations are prepared by serial dilution of these solutions in a ratio of 1:2 and a blank value without triazine is determined in each case.

Results:

3 of the 10 sheep treated with the immunogen according to the invention react well with the aforementioned heterologous POD conjugate.

The results of the two experiments using one of the selected antisera are summarized in Table 1.

By combination of antibody and conjugate according to the invention the detection sensitivity as well as the cross reaction is significantly improved.

TABLE 1

Cross reaction and detection sensitivity for antiserum S 4612

| Hapten | Measurement with homologous POD conjugate | | Measurement with heterologous POD conjugate | |
|---|---|---|---|---|
| | cross reaction % | lower detection limit (ng/l) | cross reaction (%) | lower detection limit (ng/l) |
| terbutyl-azine | 100 | 100 | 100 | 12 |
| atrazine | 4 | 1,600 | 73 | 17 |
| desethyl-terbutyl-azine | 9 | 430 | 102 | 10 |
| propazine | 8 | 620 | 26 | 24 |
| simazine | 0.9 | 4.100 | 10 | 60 |
| cyanazine | 11 | 310 | 102 | 10 |
| desethyl-atrazine | <0.3 | 9,500 | 7 | 90 |

We claim:

1. An immunological method for the determination of triazine atrazine, simazine, amedryne, propazine, terbutylazine, cyanazine, desethylterbutylazine, desethylatrazine or deisopropylatrazine by a competitive immunoassay, comprising the steps of:
    reacting a sample and a labelled triazine with a polyclonal antibody,
    binding said polyclonal antibody to a solid phase,
    separating the solid phase and any unbound labelled triazine present in a liquid phase, and
    determining any label present in the solid or liquid phase as a measure of the triazine, atrazine, simazine, amedryne, propazine, terbutylazine, cyanazine, desethylterbutylazine, desethylatrazine or deisopropylatrazine present in said sample,
        wherein said polyclonal antibody is obtained by immunization of an immunologically competent animal with a 2-chloro-4-tert.butylamino-S-triazine bound to an immunogenic carrier via the 6 position, and wherein said labelled triazine is a conjugate comprising a label and 2-chloro-4-amino-S-triazine which is bound to the label via the 6 position.

2. The method according to claim 1, wherein said polyclonal antibody is bound to said solid phase before said sample and labelled triazine are reacted with said polyclonal antibody.

3. The method according to claim 1, wherein said polyclonal antibody is bound to said solid phase after said sample and labelled triazine are reacted with said polyclonal antibody.

4. The method according to claim 1, wherein said polyclonal antibody is bound to said solid phase while said sample and labelled triazine are reacted with said polyclonal antibody.

5. The method according to claim 1, wherein said polyclonal antibody is bound to said solid phase by nucleophilic substitution.

6. The method according to claim 1, wherein said immunologically competent animal is a sheep.

7. The method according to claim 1, wherein said polyclonal antibody is bound to said solid phase by absorptive binding, covalent binding or by use of a binding pair.

8. The method according to claim 1, wherein said label is an enzyme.

9. The method according to claim 2, wherein said label is an enzyme.

10. The method according to claim 3, wherein said label is an enzyme.

11. The method according to claim 4, wherein said label is an enzyme.

12. A method for the determination of triazine, atrazine, simazine, amedryne, propazine, terbutylazine, cyanazine, desethylterbutylazine, desethylatrazine or deisopropylatrazine in a water sample, comprising the steps of:

reacting a water sample and a labelled triazine with a polyclonal antibody, binding said polyclonal antibody to a solid phase, separating the solid phase and any unbound labelled triazine present in a liquid phase, and determining any label present in the solid or liquid phase as a measure of the triazine, atrazine, simazine, amedryne, propazine, terbutylazine, cyanazine, desethylterbutylazine, desethylatrazine or deisopropylatrazine present in said sample, wherein said polyclonal antibody is obtained by immunization of an immunologically competent animal with a 2-chloro-4-tert.butylamino-S-triazine bound to an immunogenic carrier via the 6 position, and wherein said labelled triazine is a conjugate comprising a label and 2-chloro-4-amino-S-triazine which is bound to the label via the 6 position.

* * * * *